(12) United States Patent
Schieber et al.

(10) Patent No.: US 9,735,072 B2
(45) Date of Patent: Aug. 15, 2017

(54) METHOD FOR PRODUCING A PLURALITY OF MEASUREMENT REGIONS ON A CHIP, AND CHIP WITH MEASUREMENT REGIONS

(71) Applicant: Boehringer Ingelheim Vetmedica GmbH, Ingelheim am Rhein (DE)

(72) Inventors: Markus Schieber, München (DE); Heinz Schoeder, Ingelheim am Rhein (DE)

(73) Assignee: Boehringer Ingelheim Vetmedica GmbH, Ingelheim am Rhein (DE)

( * ) Notice: Subject to any disclaimer, the term of this patent is extended or adjusted under 35 U.S.C. 154(b) by 0 days.

(21) Appl. No.: 14/894,421

(22) PCT Filed: May 30, 2014

(86) PCT No.: PCT/EP2014/001462
§ 371 (c)(1),
(2) Date: Nov. 27, 2015

(87) PCT Pub. No.: WO2014/191114
PCT Pub. Date: Dec. 4, 2014

(65) Prior Publication Data
US 2016/0126151 A1 May 5, 2016

(30) Foreign Application Priority Data
May 30, 2013 (DE) .................. 10 2013 210 138

(51) Int. Cl.
*H01L 21/66* (2006.01)
*B01L 3/00* (2006.01)
(Continued)

(52) U.S. Cl.
CPC ............ *H01L 22/32* (2013.01); *B01L 3/5088* (2013.01); *G01N 27/403* (2013.01); *H01L 29/401* (2013.01); *B01J 2219/00317* (2013.01); *B01J 2219/00619* (2013.01); *B01J 2219/00635* (2013.01); *B01J 2219/00637* (2013.01); *B01J 2219/00653* (2013.01);
(Continued)

(58) Field of Classification Search
CPC ....................................... H01L 22/32
See application file for complete search history.

(56) References Cited

U.S. PATENT DOCUMENTS 5,985,551 A 11/1999 Brennan
6,183,970 B1 * 2/2001 Okano ................. B01J 19/0046
435/6.11

(Continued)

*Primary Examiner* — Evren Seven
*Assistant Examiner* — S. M. S Imtiaz
(74) *Attorney, Agent, or Firm* — David S. Safran

(57) ABSTRACT

A a chip and a method for producing the chip with a plurality of measurement regions which are provided with electrodes for electrically detecting reactions in which, in order to reliably separate the individual measurement regions from one another, a monolayer of a fluorosilane is formed on the chip surface which has strongly hydrophobic properties. Therefore, during spotting with a liquid, the drops of liquid applied by spotting can be reliably prevented from coalescing, and thus, causing mixing of the substances in the drops of liquid which are supposed to be immobilized in the measurement regions.

13 Claims, 3 Drawing Sheets

(51) Int. Cl.
*G01N 27/403* (2006.01)
*H01L 29/40* (2006.01)

(52) U.S. Cl.
CPC ... *B01L 2200/12* (2013.01); *B01L 2300/0645* (2013.01); *B01L 2300/0819* (2013.01); *B01L 2300/0861* (2013.01); *B01L 2300/0887* (2013.01)

(56) References Cited

U.S. PATENT DOCUMENTS

| | | | |
|---|---|---|---|
| 6,210,894 B1 | 4/2001 | Brennan | |
| 6,734,436 B2 | 5/2004 | Faris et al. | |
| 7,326,460 B2 | 2/2008 | Hirai | |
| 7,399,585 B2 | 7/2008 | Gau | |
| 2002/0123048 A1* | 9/2002 | Gau | B01L 3/5088 435/6.11 |
| 2003/0194709 A1* | 10/2003 | Yang | B01J 19/0046 506/43 |
| 2004/0058423 A1* | 3/2004 | Albritton | G01N 27/44743 435/173.7 |
| 2009/0131278 A1 | 5/2009 | Wagner et al. | |
| 2011/0244639 A1* | 10/2011 | Ogawa | G03F 7/0757 438/197 |

\* cited by examiner

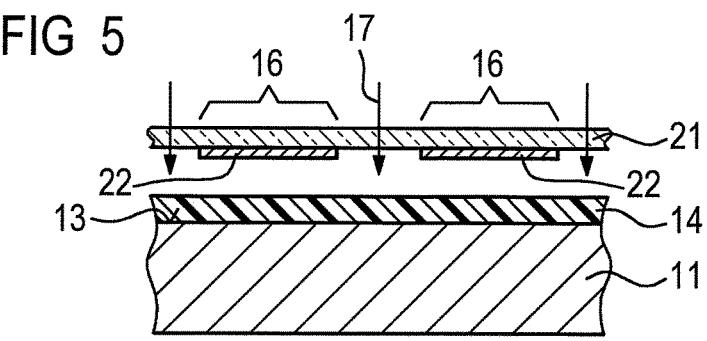
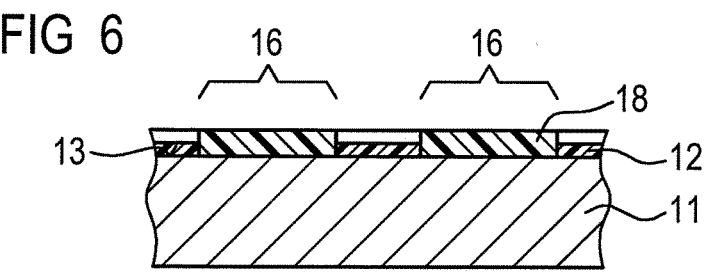
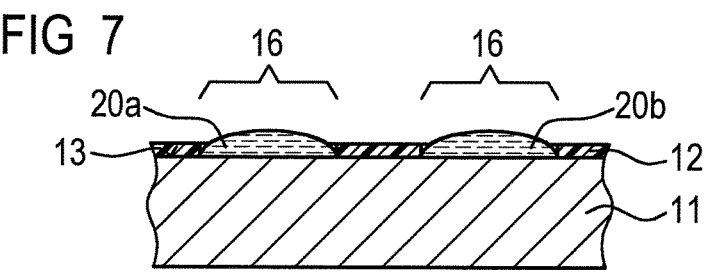
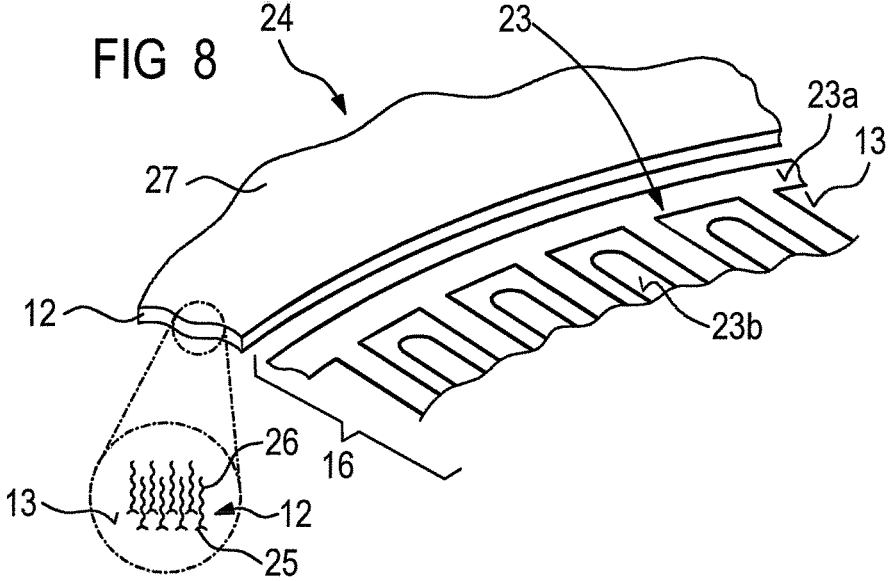

METHOD FOR PRODUCING A PLURALITY OF MEASUREMENT REGIONS ON A CHIP, AND CHIP WITH MEASUREMENT REGIONS

BACKGROUND OF THE INVENTION

Field of the Invention

The invention relates to a method for producing a plurality of measurement regions on a chip, wherein electrically contactable electrode pairs are structured on the chip in each of the measurement regions and wherein the measurement regions are formed by producing a compartmental structure which separates the measurement regions from one another.

Description of Related Art

Moreover, the invention relates to a chip having a plurality of electrically addressable measurement regions, wherein a compartmental structure which separates the measurement regions from one another is provided on the surface of the chip.

A chip of the kind described hereinbefore and a method of producing it is known, for example, from U.S. Patent Application Publication 2009/0131278 A1. The chip is a silicon-based chip on the surface of which are provided a plurality of electrode pairs by metalizing and structuring. These pairings are in a two-dimensional array, preferably a chessboard arrangement. The electrode arrangements consist of electrode strips meshing with one another which ensure that the two electrodes of the electrode arrangement are adjacent to one another over a long distance.

The measurement regions are provided for functionalizing with certain biologically active substances. These may be, for example, antibodies which react chemically to specific antigens, these chemical reactions being electrically detectable by means of the electrode arrangement. Functionalization is carried out by a so-called spotting process, in which each measurement region is acted upon by another, e.g., water-based solution. The molecules responsible for the functionalization on the corresponding measurement regions are thereby immobilized. It is crucially important that the different liquids in the individual measurement regions are not mixed with one another, to ensure that only one type of relevant molecules is present on each measurement region.

To prevent the liquids of adjacent spots from being mixed together, it is proposed according to from U.S. Patent Application Publication 2009/0131278 A1 that mechanical barriers in the form of small walls may be provided between the individual measurement regions. The surface of the chip is thus divided into different compartments of a box, so to speak, the liquids each being "poured" into one of these compartments during the spotting process. However, it should be taken into consideration that the compartments present on the chip surface are of an order of magnitude in the µm range. Therefore, the effect of the mechanical boundaries comes up against its limits. As a result of the surface tension of the solvent, such as water, it may happen that in spite of the mechanical boundaries the liquids of adjacent measurement regions combine and thus the relevant functional molecules are mixed together.

SUMMARY OF THE INVENTION

The object of the invention is to provide a method for producing a plurality of measurement regions on a chip, as well as a chip which can be produced by this method in particular, while at least substantially preventing liquids from mixing together during the spotting process.

The above problem is solved by a method and a chip as described herein.

It goes without saying that features, embodiments, advantages and the like which are mentioned hereinafter only in connection with one aspect of the invention, to avoid repetition, nevertheless also apply accordingly to the other aspects of the invention.

It also goes without saying that in the statements of values, numbers and ranges provided hereinafter, the values or ranges specified should not be interpreted in a restrictive capacity; the skilled man will understand that deviations may occur from the specified ranges and figures, as a result of individual cases or in relation to particular applications, without departing from the scope of the present invention.

Moreover, it is the case that all the values or parameters or the like specified hereinafter may be determined or ascertained by standardized or explicitly stated methods of determination or by methods of determination which are familiar to the skilled man. Subject to this, the present invention will now be described in more detail.

According to one aspect of the present invention, the formation of the compartmental structure is preferably carried out using the following process steps. First, hydrophilic properties are produced in the measurement regions. This is a necessary prerequisite for wetting the measurement regions with a hydrophilic liquid. Generally, the functional molecules are dissolved in water, and for this reason the hydrophilic properties of the measurement regions are of supreme importance. Moreover, the method according to the invention comprises producing hydrophobic wetting properties on the surface of the chip outside the measurement regions by applying a self-organized monolayer consisting of a fluorosilane compound. Examples of possible fluorosilane compounds include Teflon (polytetrafluoroethylene or PTFE). For example, (tridecafluoro-1,1,2,2-tetrahydrooctyl) trichlorosilane $C_8H_4Cl_3F_{13}Si$ may be used. Advantageously, the hydrophobic effect of this monolayer is far more effective than a mechanical barrier. Owing to the fact that the chip surface between the measurement regions is virtually impossible to wet with hydrophilic liquids, a safety interval is produced between the individual spots of the functional liquids, which effectively prevents mixing. Therefore, reliably functionalized chips can advantageously be produced by the method according to the invention.

According to another aspect of the present invention, in particular, a chip is proposed in which the compartmental structure is formed from a self-organized (self-assembling) monolayer, consisting of a fluorosilane compound, which covers the chip surface outside the measurement regions.

A monolayer is formed when only one layer of molecules is formed on the chip surface. The self assembly of the monolayer is caused by the structure of the fluorosilane compound used. The fluorosilane molecules comprise a trichlorosilane group which has a high affinity for silicon, which is why this group is provided on the surface of the chip. The remainder of the molecules are then distanced from the surface, and form a surface which is comparatively hydrophobic. This hydrophobic action on the surface is advantageously highly effective.

According to an embodiment of the method according to the invention, the method is carried out using the following steps in the order specified, in order to form the compartmental structure. First, a fluorosilane compound is vapor-deposited on the chip surface as a monolayer. This takes place in a vacuum atmosphere. CVD or PVD processes may be used. Then a photo-structurable coating is applied to the chip surface. This initially covers the whole of the chip surface. Next, the measurement regions are illuminated through a suitable mask. By developing the photo-structurable coating, a photo-structured coating is formed in which the measurement regions can be exposed. In the measurement regions thus exposed, hydrophilic properties are generated so that the aqueous solutions can be spotted onto them. Finally, the photo-structurable coating is removed.

According to an alternative embodiment of the invention, the method for forming the compartmental structure may also be carried out using the following process steps in the order specified. First the hydrophilic properties are generated over the entire chip surface. Then a photo-structurable coating is applied to the chip surface. This can be photo-structured by illuminating the surface of the chip outside the measurement regions. A photo-structured coating is produced by developing the photo-structurable coating, the measurement regions being covered by the photo-structured coating. Then a fluorosilane compounds is vapour-deposited in a monolayer on the surface of the chip, in the manner already mentioned. Finally, the photo-structured coating is removed.

The two alternative processes have the major advantage that the individual production steps are well known per se and can therefore be carried out with considerable process reliability. Therefore, by improving the process reliability, high quality results are advantageously obtained.

According to another embodiment of the process, it is provided that the production of the hydrophilic properties is carried out in an oxygen plasma or by dry etching. These methods, which are conventional in the processing of wafers, are also advantageously carried out with high process reliability.

According to a further embodiment of the invention it is provided that, after the end of the process steps as described above, the processed chip surface is cleaned. In this way the chip surface can be prepared for a subsequent spotting process. Contamination is advantageously eliminated so that after spotting no measurement errors occur as a result of a contaminated surface of the measurement regions. The cleaning of the processed chip surface may form the end of the preparation of the chips. These chips are then packaged so that no further cleaning of the chip surface is required. The user will then only remove the packaging just before the spotting process is carried out. Alternatively, it is, or course, also possible for the cleaning to be carried out by the user at the last possible moment before the spotting process.

The cleaning is preferably carried out by a wet chemical method. The use of a piranha solution is recommended. This consists of a mixture of hydrogen peroxide and sulphuric acid and constitutes a highly effective compound for cleaning the surface. Advantageously, the monolayer of fluorosilane compounds is sufficiently chemically stable to withstand this cleaning step.

According to a further embodiment of the invention it is also possible for the functionalization of the measurement regions by a spotting process to be carried out immediately after the cleaning has taken place. In this case the user is provided with the already functionalized chips. This is advantageous in analytical processes which are very often used as standard, as the chips can be functionalized in large numbers immediately after manufacture. This satisfactorily prevents contamination during the process.

According to another aspect of the present invention, a method for producing a chip having a plurality of electrically addressable measurement regions or for producing a plurality of measurement regions on a chip is proposed, in which electrically contactable electrode pairings are structured in each of the measurement regions on the chip and the measurement regions are formed by producing a compartmental structure which separates the measurement regions from one another.

The formation of the compartmental structure comprises the production of hydrophobic wetting properties on the surface of the chip outside the measurement regions. Moreover, the formation of the compartmental structure may include the production of hydrophilic properties in the measurement regions.

Furthermore, according to an aspect of the present invention which can be achieved independently, the measurement regions are provided with a protective coating at least substantially until the chip is incorporated in an electric component. By the expression "until the chip is incorporated" is meant the process step in the manufacture of the chip in which removal of the protective coating makes sense. This may be immediately before the spotting process, but may also, for example, be immediately after the cutting of the wafer from which the chip is made, or after the electrical contacting (bonding) of the (individual) chip.

The use of a protective coating which at least substantially covers the measurement regions makes further processing of the chip easier. The chip, or the wafer from which the chip is made, may for example be divided up or electrically connected or provided with passivation on the outside or cast, without any risk of the delicate measurement regions or areas of the chip vapor-coated with metals such as gold, being exposed to mechanical, thermal or chemical stresses and being damaged or even destroyed.

Within the scope of the present invention, particularly good results are obtained if the protective coating is a photo-structured coating or a photoresist. Photo-structured coatings are generally obtainable from photo-structurable coatings. By a photo-structurable coating is meant, within the scope of the present invention, a coating the aggregate state and/or chemical nature of which is altered by the effects of electromagnetic radiation, particularly UV radiation, thus producing a photo-structured coating. In particular, it is provided in this context that only the regions of the photo-structurable coating which are exposed to the electromagnetic radiation are subject to change. The change in the protective coating induced by the effect of electromagnetic radiation may be in particular such that the coating becomes fixed or liquefies, is chemically cured, i.e. cross-linked, or polymeric structures are destroyed. Thus, by the use of masks and UV radiators, for example, structures can thus be produced on the surface of the chip.

In this context it may be envisaged that the photo-structured coating contains a photoresist or is a photoresist. Photoresists which usually cure under the effect of UV radiation are known per se to the skilled man and are commercially available in large numbers.

Within the scope of the present invention it is preferable if the photo-structured coating is a photoresist which is also used within the scope of rendering the chip surface hydrophobic. In this way, time, materials and equipment can be saved within the scope of the present invention, as the photo-structured coating applied in the course of producing the hydrophobic finish, particularly the photoresist, also remains on the measurement regions for protecting the measurement regions even after the hydrophobic finish has been applied and continues to protect these regions up to the time of installation or until the processing of the chip has been complete.

If a photo-structured coating is used as a protective coating for the within the scope of the present invention, it is preferable if the photo-structured coating, particularly the photoresist, is chemically and/or physically stable at least for short periods at temperatures up to 150° C., particularly 200° C., preferably 250° C., preferably 300° C. During the processing of the chip, for example during the cutting process or installation into devices, it may happen over and over again that the chip is subjected to thermal peaks, i.e. short-lived thermal stresses. In this case, the photo-structured coating or the photoresist must not decompose chemically, nor can the chemical or physical nature change so that the measurement regions are no longer adequately protected, or the coating is no longer removable at a later stage.

For this reason, the protective coating or the photo-structured coating applied should be sufficiently thermally stable, particularly at the temperature peaks which occur briefly during the processing of the chip.

Thermally resistant photo-structured coatings or photoresists of this kind are advantageously formed on the basis of polyamide, within the scope of the present invention. Polyamide-based photoresists often have a decidedly high thermal stability of up to 400° C. and may furthermore be hydrophobic.

Generally, the hydrophobic treatment is carried out within the scope of the present invention by applying a hydrophobic coating to the chip. In this context, it may be that the hydrophobic coating is applied to the chip in the form of a layer of lacquer or a monolayer. If the hydrophobic coating is applied as a layer of lacquer, this may refer particularly to photo-structured coatings, particularly photoresists, which cure or depolymerise or are destroyed by electromagnetic radiation, particularly UV radiation. When, within the scope of the present invention, the hydrophobic coating is formed by a photoresist, and in particular the photoresist is applied to the chip by one of the methods described above, there is no need for any further hydrophobic treatment of the surface of the chip. In this case, the hydrophobic photoresist remains outside the measurement regions on the chip and is not removed again. If, on the other hand, the hydrophobic coating is formed by a monolayer, it has proved satisfactory within the scope of the present invention if the monolayer is applied as a self-assembling monolayer. Monolayers produce particularly sharply delimited hydrophobic regions on the chip.

Similarly within the scope of the present invention it may also be provided that the hydrophobic treatment is carried out by reacting with reactive chemical compounds. Preferably, the reactive chemical compounds used within the scope of the present invention are silanes, particularly alkylsilanes and/or fluorosilanes. When alkylsilanes are used within the scope of the present invention, it has proved suitable to use trialkylsilanes or silazanes as alkylsilanes, preferably trimethylchlorosilane and/or hexamethyldisilazane. If, on the other hand, fluorosilanes are used within the scope of the present invention, it has proved satisfactory to use partially fluorinated or perfluorinated silanes, most preferably tridecafluoro-1,1,2,2-tetrahydrooctyl-trichlorosilane.

The use of fluorosilanes is particularly preferred as they have not only outstanding hydrophobic properties but also excellent chemical resistance.

For further details on the process according to the invention, reference may be made to the foregoing remarks on the other aspects of the invention which apply equally to the method according to the invention.

In respect of other details regarding the method according to the invention, reference may be made to the remarks concerning the other aspects of the invention which apply equally to the method according to the invention.

Finally, according to a fourth aspect of the present invention, the invention also relates to a chip having a plurality of measurement regions, which can be obtained by the method described hereinbefore.

For further details on the chip according to the invention, reference may be made to the foregoing remarks on the other aspects of the invention which apply equally to the chip according to the invention.

Further details of the invention are described hereinafter by reference to the drawings. Identical or corresponding elements of the drawings have been given the same reference numerals in the figures and their explanations are only repeated where there are differences between the individual figures.

BRIEF DESCRIPTION OF THE DRAWINGS

FIGS. 5 to 7 show selected manufacturing steps of another embodiment of the method according to the invention, FIG. 8 shows a detail of the surface of the chip of an embodiment of the chip according to the invention as a three-dimensional view.

DETAILED DESCRIPTION OF THE INVENTION

Figure 1:
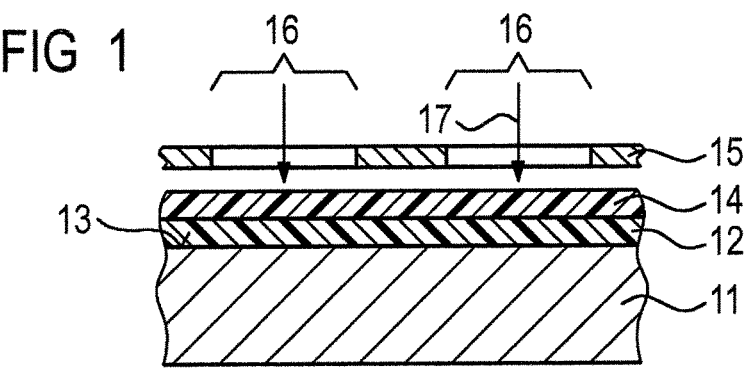
FIGS. 1 to 4 show selected steps of a first embodiment of the method according to the invention.

FIG. 1 shows the detail of a chip 11 made of silicon. However, the chip 11 may also be made of a different material.

Figure 9:
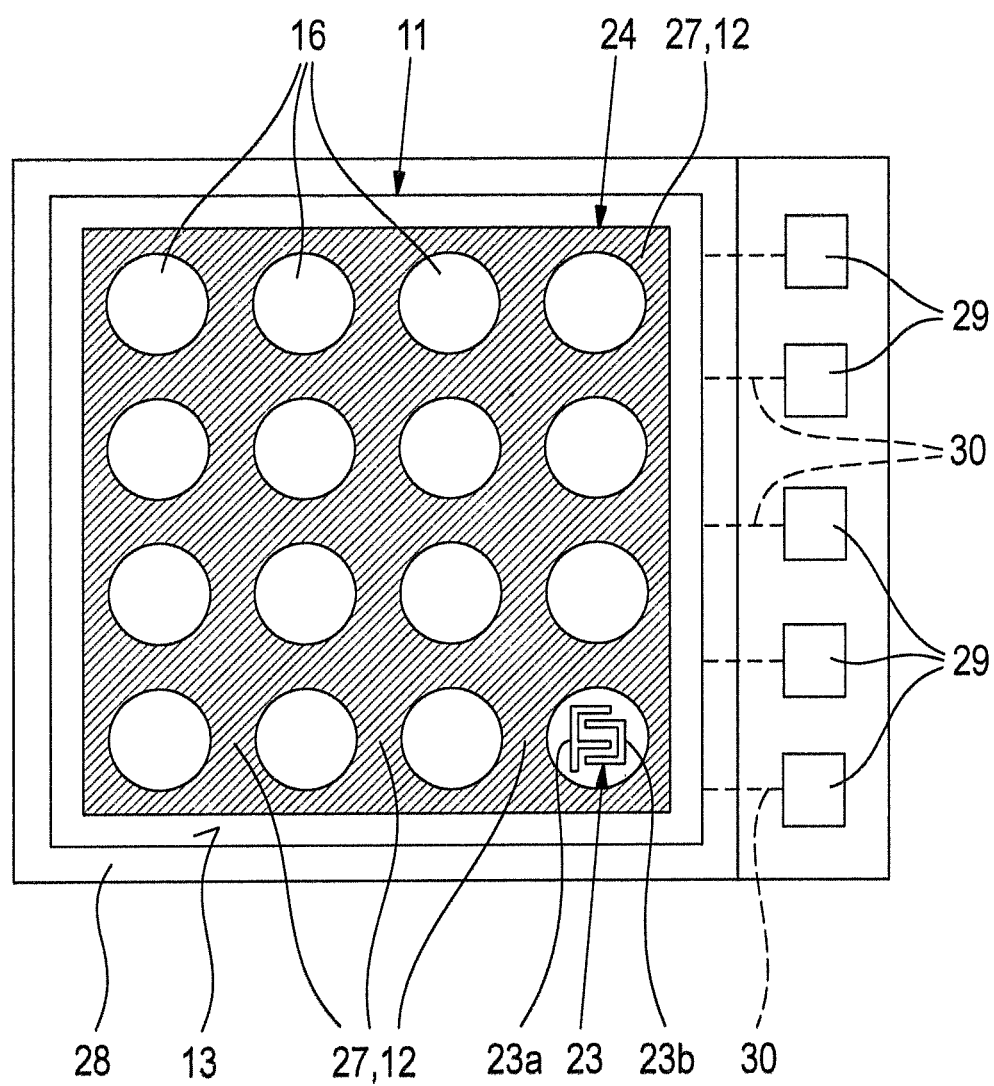
FIG. 9 shows a schematic representation of the chip in the connected and installed state.

Particularly preferably, the chip 11 comprises or contains electronic circuits and/or electrode arrangements 23 not shown in FIG. 1 (cf. FIGS. 8 and 9).

The chip 1 preferably has a hydrophobic coating 12 which may take the form of a monolayer and/or may preferably contain or be formed from a fluorosilane compound.

Preferably, a fluorosilane compound, particularly as described above, has first been vapour deposited on the chip 11 in a desiccator, in the course of which the fluorosilane compound has formed a self-assembled monolayer 12 on the chip surface 13. After this, a photo-structurable coating 14 has been applied to the monolayer 12. Using a perforated mask 15, the regions that are intended to form the measurement regions 16 subsequently are illuminated with light 17 (cf. also FIG. 4).

Figure 2:
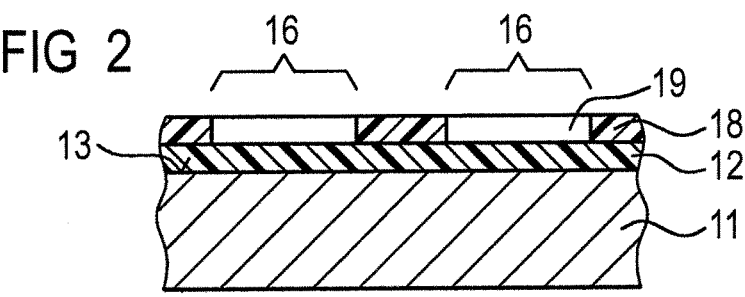

FIG. 2 shows the photo-structured coating 18 after the photo-structurable coating 14 has been developed. In this way, the hydrophilic regions which subsequently produce the measurement regions 16 are defined. They appear as windows 19 in the photo-structured coating 18.

Figure 3:
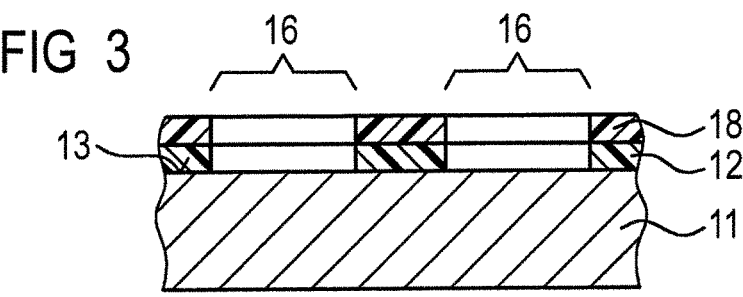
Figure 4:
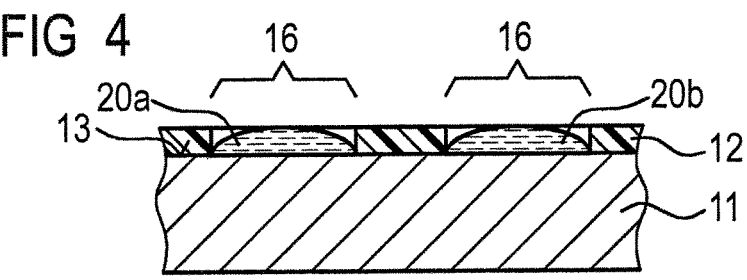

FIG. 3 shows how the hydrophilic regions have been produced in the oxygen plasma. The monolayer 12 has been removed in the region of the windows 19, apart from the chip surface 13. In this way the hydrophilic measurement regions 16 are formed. Then the photo-structured coating 18 has also to be removed from the monolayer 12. This can be seen in FIG. 4. FIG. 4 also shows how different liquids 20a, 20b are applied to the measurement regions 16 in order to functionalize these measurement regions (spotting method). In this way the finished functionalized chip 11 is produced.

The method according to FIGS. 5 to 7 also works with a photo-structurable coating 14 and a hydrophobic coating or a monolayer 12 (cf. FIG. 6). However, the order of application of these two coatings is precisely reversed, compared with the method described according to FIGS. 1 to 4. According to FIG. 5, first of all, the photo-structurable coating 14 is applied to the surface 13 of the chip 11.

For structuring the photo-structurable coating 14, an illuminating mask 21 is preferably used which consists of a transparent sheet and has a lightproof coating 22 in the region of what will subsequently be the measurement regions 16. The photo-structurable coating 14 is structured by means of the light 17.

As can be seen from FIG. 6, the photo-structured coating 18 remains in the measurement regions 16, while the surrounding areas have been exposed right down to the surface of the chip 13. These regions are then coated with the hydrophobic coating or self-assembling monolayer 12, particularly of fluorosilanes.

As can be seen from FIG. 7, the photo-structured coating 18 is then removed, exposing the measurement regions 16. These are located directly on the chip surface 13. The functionalizing of the measurement regions 16, as described previously, is carried out by a spotting process in which the liquids 20a, 20b are applied.

Alternatively, the measurement regions 16 may also only be exposed later. The measurement regions 16 are then protected by the photo-structurable coating 14 or the photo-structured coating 18, i.e., by a protecting coating, or by a photoresist or the like which forms it, for example, until the chip 11 has been separated from other chips (not shown) of a wafer or the like, and/or until the chip 11 has been electrically connected (bonded) and/or provided with a passivation layer on the outside and/or cast into position or installed in a housing.

To form the photo-structurable coating 14 it is particularly preferable to use a photoresist. Particularly preferably, a polyamide-based photoresist is used, especially on account of its thermal stability.

According to another alternative, the structurable or structured coating 14, 18 or the photoresist is preferably used instead of the monolayer 12 or fluorosilane compound to form the hydrophobic layer 12 or compartmental structure 24. The photo-structurable coating 14, as indicated in FIG. 5, then forms the hydrophobic layer or coating in the desired regions and hence the compartmental structure 24 or intermediate regions 27. The method is thereby simplified, as preferably only the coating 14 or the photoresist has to be removed to form the measurement regions 16, i.e. there is no need to apply a second coating. In this case the photoresist is then preferably of a correspondingly hydrophobic nature or can be rendered hydrophobic by an alternative method.

FIG. 8 shows a detail of the edge of a measurement region 16 on the chip surface 13. The measurement region 16 comprises an electrode pairing or arrangement 23 which preferably consists of a first electrode 23a and a second electrode 23b. These electrodes preferably comprise fingers which preferably mesh with one another. This electrode arrangement 23 reacts with great sensitivity to the fact that functional molecules (not shown in detail) which are immobilized in the measurement region 16, react with molecules that are to be detected.

The measurement region 16 is also surrounded by a compartmental structure 24, only a detail of which is shown. Part of this detail is shown on a larger scale, showing that the compartmental structure 24 is preferably formed from the layer or monolayer 12. This consists particularly of molecules of the fluorosilane compound, these molecules being docked with their functional group 25 on the surface 13 of the chip 11, whereas the molecular residue 26 which produces the highly hydrophobic properties of the monolayer 12 projects upwardly or away from it.

Preferably, the compartmental structure 24 or the hydrophobic coating 12—particularly on its free surface—forms a hydrophobic intermediate region 27 between the (adjacent) measurement regions 16, so that liquids 20a, 20b not shown in FIG. 8 do not flow into adjacent measurement regions 16 or mix or combine fluidically with adjacent liquids during spotting, i.e. during the application of drops of liquid to the measurement regions 16, particularly for immobilizing scavenger molecules or the like (not shown).

The compartmental structure 24 or the hydrophobic coating 12 or the respective intermediate region 27 is therefore preferably hydrophobic, particularly strongly hydrophobic.

Particularly preferably, the contact angle of the compartmental structure 24 or the hydrophobic coating 12 or the intermediate regions 27 with water is at least substantially 90°, preferably more than 120°, most preferably more than 150°, in each case measured under normal conditions with distilled water.

FIG. 9 shows, in a highly diagrammatic plan view, the proposed chip 11 in the connected, installed state, or the chip 11 with or in a housing 28.

Preferably, the chip 11 together with other chips 11 is produced in a conventional process, for example by the CMOS method, on a common carrier or substrate, particularly a so-called wafer. Then the chips 11 are separated from one another, connected electrically and preferably installed, particularly in an associated housing 28 or the like.

In the embodiment shown, the chip 11 is preferably electrically connected to contact surfaces or terminals 29, particularly by electrical connections 30 indicated by dashed lines. This is only schematically shown here. The electrical connection of the chips 11 is usually referred to as bonding.

In the installed state, at least the measurement regions 16 are accessible for receiving samples (not shown) that are to be measured.

FIG. 9 shows the compartmental structure 24 which with its intermediate regions 27 or hydrophobic layers 12 (completely) surrounds the measurement regions 16 and/or separates them from one another. In particular, a lattice-like or honeycomb-shaped structure is formed, each measurement region 16 preferably being annularly defined.

As already mentioned, the measurement regions 16 may be covered or protected by a protective layer, particularly a coating 14, particularly preferably of photoresist. This protective coating is then preferably not removed until after the cutting or division of the chips 11 and/or after the electrical connection and/or installation of the chip 11 in question. However, it is also possible to expose the measurement regions 16 earlier.

If the removal of the protective layer does not take place until after installation, the protective layer is particularly preferably configured to be of sufficient thermal stability. In fact, for installation, the chip 11 is cast into position, in particular. Because of the temperatures occurring, a conventional photoresist may harden. This would at least make it difficult, if not completely impossible, to remove it from the measurement regions 16 at a later stage. Therefore, preferably, a photoresist is used which is sufficiently thermally stable without hardening. A polyamide-based photoresist is particularly suitable for this purpose.

FIG. 9 schematically shows an electrode arrangement 23 in only one measurement region 16, namely in the lower right-hand measurement region 16. In particular, electrode arrangements 23 of this kind which are preferably identical or similar, are formed or arranged in all the measurement regions 16.

The electrode arrangements 23 are preferably formed before the production or application of the compartmental structure 24.

The electrode arrangements 23 are preferably located at least substantially in the chip surface 13 on which the measurement regions 16 are formed and the compartmental structure 24 is created.

The chip surface 13 is preferably configured to be at least substantially flat and/or preferably constitutes a flat side of the chip 11.

In the embodiment shown, the hydrophobic layers 12 or intermediate regions 27 preferably adhere to one another and/or form a cohesive lattice. However, they may also form separate regions or portions on the chip surface 13 which surround or enclose one or more measurement regions 16.

Preferably, different molecules for detection may be detected in the measurement regions 16 by means of the electrode arrangements 23. Corresponding detection signals are emitted electrically, in particular, by the chip 11 or can preferably be interrogated electrically.

Preferably, the compartmental structure 24 is raised relative to the at least substantially flat ship surface 13.

Preferably, the compartmental structure 24 surrounds each measurement region 16 completely or annularly with the hydrophobic layer 12 of the hydrophobic intermediate region 27.

In particular, the compartmental structure 24 or hydrophobic layer 12 or monolayer or the intermediate region 27 is of lattice-like or honeycomb-shaped configuration.

The compartmental structure 24 or hydrophobic layer 12 or intermediate regions 27 is or are preferably embodied as a flat and/or planar coating.

Preferably, the compartmental structure 24 or hydrophobic layer 12 or the intermediate region 27 is smaller in height than width. Particularly preferably, the width between two adjacent measurement regions 16 is greater than the height relative to the chip surface 13 carrying the measurement regions 16 by a factor of at least 5, preferably by a factor of at least 10.

Particularly preferably, the height of the compartmental structure 24 or hydrophobic layer 12 or the hydrophobic intermediate region 27 is less than 2 µm, more particularly less than 1 µm, and/or more than 10 nm, particularly more than 100 nm.

Particularly preferably, the intermediate regions 27 have a width between the measurement regions 16 of more than 10%, particularly more than 20%, particularly preferably about 50% or more, of a measurement region 16.

Particularly preferably, the intermediate regions 27 have a width between the measurement regions 16 of more than 5 µm, particularly more than 10 µm or 20 µm, particularly preferably more than 50 µm.

The measurement regions 16 preferably have a width or an average diameter of more than 50 µm, particularly more than 100 µm, and/or less than 500 µm, preferably less than 300 µm, particularly less than 200 µm, most particularly preferably about 120 to 180 µm.

Preferably, during the so-called spotting, drops of liquid 20a, 20b are applied to the individual measurement regions 16, particularly each having a volume of 1,000 to 2,000 pl, while the hydrophobic layers 12 or intermediate regions 27 ensure that the drops of liquid 20a, 20b remain in place on the respective measurement region 16 and do not mix with adjacent drops of liquid 20a, 20b and/or do not flow into an adjacent measurement region 16.

The above-mentioned spotting may theoretically be carried out as desired, either before or after the division of the chips 11 and/or the electrical connection and installation of the chip 11 in question. Preferably, the spotting takes place after the connection and installation of the chips 11.

The spotting or application of drops of liquid 20a, 20b serves, in particular, only to functionalize the individual measurement regions 16, i.e., particularly to precipitate or bind special molecules for trapping or reacting with molecules that are to be detected in a sample. The drops of liquid are removed again, in particular, after a desired immobilization or binding of the special molecules. Thus, spotting also serves in particular to prepare the chip 11 or the measurement regions 16.

The sample liquid itself, containing molecules that are to be measured or detected, is subsequently applied to the chip 11 or the measurement regions 16—for example over the entire surface and/or using a membrane which covers, as flatly as possible, the measurement regions 16 with the sample liquid located thereon—when the chip 11 is used correctly. The membrane may interact with the compartmental structure 24, in particular may lie on it, in order to distribute the sample liquid over the measurement regions 16 and/or to achieve fluidic separation of the sample liquid in the various measurement regions 16 from one another.

However, alternatively, it is also possible to apply one or more samples that are to be measured to the previously functionalized measurement regions 16 by spotting.

Individual aspects and features of the various embodiments, variants and alternatives may also be implemented independently of one another, but also in any desired combination.

What is claimed is:

1. Chip having a plurality of electrically addressable measurement regions, wherein a compartmental structure separates the measurement regions from one another on the chip surface, wherein the compartmental structure has a hydrophobic layer, wherein the hydrophobic layer contains a photoresist or is a photoresist and wherein the chip surface is planar and the compartmental structure is raised relative thereto.

2. Chip according to claim 1, wherein the photoresist is a polyamide-based photoresist.

3. Chip according to claim 1, wherein electrically contactable electrode pairings are structured in each of the measurement regions on the chip.

4. Chip according to claim 1, wherein the compartmental structure surrounds each measurement region completely or annularly with a hydrophobic layer or a hydrophobic intermediate region.

5. Chip according to claim 1, wherein the compartmental structure or hydrophobic layer is of lattice-shaped and/or honeycomb-shaped configuration.

6. Chip according to claim 1, wherein the compartmental structure or hydrophobic layer is smaller in height than in width and the width between two adjacent measurement regions is greater than the height relative to the chip surface carrying the measurement regions by at least a factor 5.

7. Chip according to claim 1, wherein the compartmental structure or hydrophobic layer forms hydrophobic intermediate regions between the measurement regions.

8. Chip according to claim 7, wherein the intermediate regions between the measurement regions have a width between the measurement regions of more than 20%, of a measurement region.

9. Chip according to claim 7, wherein the intermediate regions have a width between the measurement regions of more than 5 µm.

10. Chip according to claim 1, wherein the compartmental structure or the hydrophobic layer has a contact angle with water of at least 90°.

11. Chip according to claim 1, wherein the compartmental structure or hydrophobic layer is at least briefly chemically and physically stable at temperatures up to 150° C.

12. Method for producing a chip having a plurality of electrically addressable measurement regions, comprising:
    structuring electrically contactable electrode pairings on the chip in each of the electrically addressable measurement regions, and
    forming the measurement regions by producing a compartmental structure that comprises a hydrophobic layer that separates the measurement regions from each other,
    wherein the hydrophobic layer is produced by applying a hydrophobic coating in the form of photoresist to the chip, resulting in a compartmental structure that is raised relative to a planar chip surface.

13. A chip having a plurality of electrically addressable measurement regions produced by the process of claim 12.

* * * * *